United States Patent [19]

Judet

[11] 4,098,269
[45] Jul. 4, 1978

[54] ARTICULATED FIXATION DEVICE TO HOLD UNALIGNED BONY PARTS IN A FIXED RELATIVE POSITION

[76] Inventor: Robert Judet, 42 Avenue Bugeaud, Paris, France

[21] Appl. No.: 781,050

[22] Filed: Mar. 24, 1977

[30] Foreign Application Priority Data

Mar. 26, 1976 [FR] France .............................. 76 08823

[51] Int. Cl.² .......................... A61F 5/04; A61B 17/18
[52] U.S. Cl. .................................. 128/92 A; 128/84 B
[58] Field of Search .............. 128/92 A, 92 R, 92 E, 128/92 EB, 84 R, 84 B, 85, 83

[56] References Cited

U.S. PATENT DOCUMENTS

| 2,251,209 | 7/1941 | Stader | 128/92 A |
| 2,333,033 | 10/1943 | Mraz | 128/92 A |
| 2,497,626 | 2/1950 | Persall | 128/92 A |
| 3,709,219 | 1/1973 | Halloran | 128/92 A |

FOREIGN PATENT DOCUMENTS

| 1,569,090 | 5/1969 | France | 128/92 A |
| 2,274,266 | 1/1976 | France | 128/92 A |
| 580,406 | 8/1958 | Italy | 128/92 A |

Primary Examiner—Ronald L. Frinks
Attorney, Agent, or Firm—Darby & Darby

[57] ABSTRACT

An articulated fixator for setting bones having a toggle piece to which is connected a brace piece. A pair of bars, each of which is to be fastened to a respective piece of the bone to be set, is pivotally connected to said toggle piece. A pair of stays are provided, each of which has one end pivotally connected to the end of the brace piece remote from the toggle piece. Each stay has a slot therein and a connection is made between a stay and a respective bar at a selected point along the length of the slot of a stay. In this manner two independent angles of fixation can be obtained.

7 Claims, 3 Drawing Figures

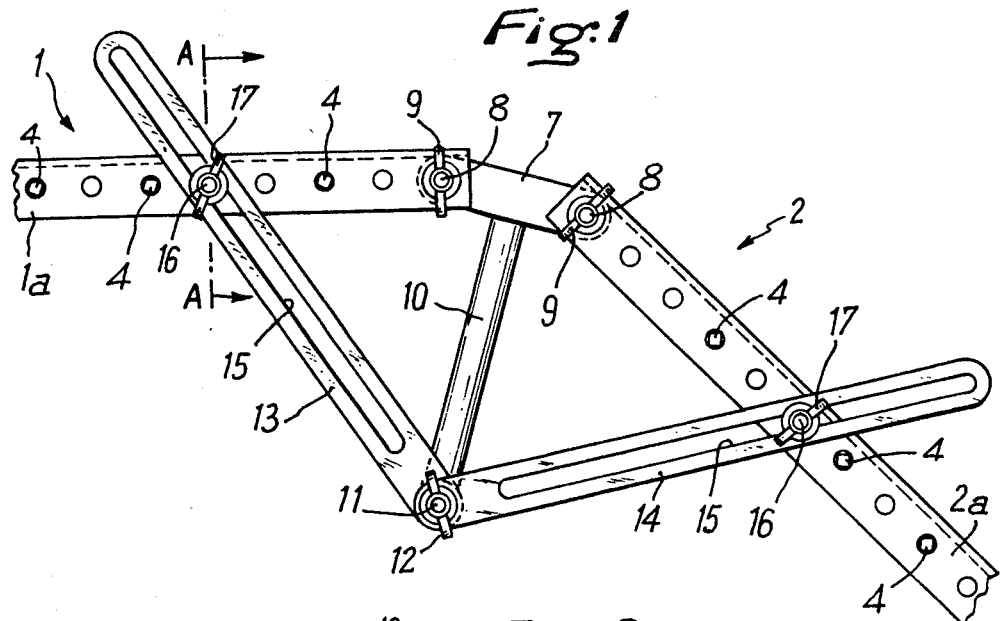
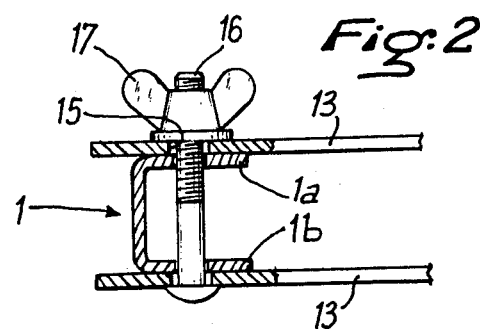
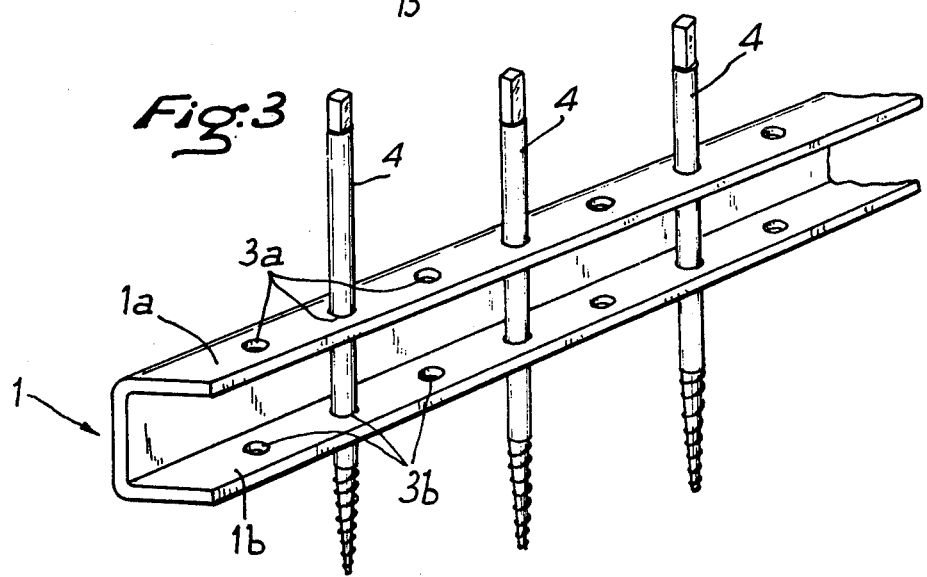

ARTICULATED FIXATION DEVICE TO HOLD UNALIGNED BONY PARTS IN A FIXED RELATIVE POSITION

In order to maintain two bony parts, such as, for example, two pieces of a broken bone, in a fixed position relative to one another, it is known to use a device called an "external fixator" having a prop connected to the two bone fragments by pins planted in the said fragments. This prop is formed by a bar, rigid in itself, having a U-shaped profile piece, whose two flanges are perforated at regular intervals with holes through which the said pins pass.

This device has a drawback in that it can be used only to hold bony parts which have to be aligned, which limits its use considerably. For example, these devices cannot be used to immobilize a femur relative to the iliac bone of the pelvis.

Articulated external fixators are also known but in the known devices the pins in each group are borne on a very short prop, and the two props are articulated with respect to one another by a ball-joint device. These external fixator devices do not allow a translation of one of the props at the end of the fixation operation, a thing which is absolutely necessary in certain cases.

The object of the present invention is an improvement in external fixators of the type with a U-shaped profile piece, which makes for very solid and very stable fixations, this improvement making it possible to displace one or the other of the props, parallel to itself, after the pins are in place.

The object of the present invention is an improvement in external fixators of known type, which utilizes two bars of U-shaped profiles, whose flanges are equipped with a plurality of holes designed to receive pins planted in the bony parts. An intermediate piece is provided to which each of the said bars is articulated about an axis having locking means. A brace is provided perpendicular to the intermediate piece and solid therewith. Two stays are used, each articulated on the one hand to the end of the brace about an axis having locking means, and on the other hand to either of the bars bearing the pins.

Preferably, the axes of articulation are formed by threaded rods or bolts equipped with nuts in such a way that when the nuts are unscrewed, the pieces may pivot around the said axes, and that they will be locked on one another when the nuts are retightened.

By way of non-limiting example, and to facilitate understanding of the invention, we have represented, in the attached drawings:

FIG. 1 is a plan view of an embodiment of the invention;

FIG. 2 is a detailed view in section along A—A of FIG. 1; and

FIG. 3 is a detailed view illustrating the manner of fixation of the bars.

Referring to these figures the articulated external fixator includes two fixation bars 1 and 2. Each bar has a U-shaped profile whose two flanges 1a and 1b (2a and 2b) have a plurality of regularly spaced holes 3a and 3b, the holes 3a and 3b being strictly in alignment. In each pair of holes 3a—3b, a pin 4 is introduced whose one end 5 has a thread, and the other end 6 a square allowing a wrench to engage on the pin in such a way that the pins 4 can be screwed into the bony part to be immobilized.

The two bars 1 and 2 are both articulated to an intermediate piece 7 forming a toggle joint. Bar 1 is articulated to piece 7 at an axis defined by a bolt 8 having a threaded end on which a nut 9 is engaged which, in the example represented, is a wing nut. Bar 2 is articulated to piece 7 by identical means. Thus, when either of the nuts 9 is unscrewed, bar 1 or 2 can pivot freely, and when the respective nut 9 is tightened, the bar is rigidly connected to piece 7.

The toggle joint 7 is solid with a brace 10 extending perpendicularly to the plane defined by the two axes of articulation 8 of the toggle joint 7. At its end, brace 10 has a hole in which there is a threaded rod 11 analogous to bolt 8 and like it, having a nut 12.

On the axis defined by rod 11 are articulated two stays 13 and 14. Preferably each stay 13 or 14 has an opening, or slot, 15 extending over practically the full length of the stay. The width of opening 15 is equal to the diameter of holes 3a and 3b so that the opening 15 of stays 13 and 14 are traversed by a threaded bolt 16 equipped with a nut 17. Preferably, pins 4 and threaded bolts 8 and 11 have the same diameter.

In utilizing the invention, a bony part (not represented) is solidly attached with bar 1 by means of pins 4. Then, in identical fashion, another bony part is solidly attached with bar 2 by means of pins 4. The angle and the relative position of the two bars 1 and 2 is now determined with precision and they can be immobilized in absolutely rigid fashion by screwing nuts 9, 12 and 17.

It is possible, in case of difficulty or lack of space, to replace one of the bolts 16 and one of the bolts 8 by a pin. However, more than two locking bolts should not be eliminated in a given triangulation since the system will then not be rigid enough.

The presence of toggle joint 7 with two articulations make possible slight displacements of bars 1 and 2, while keeping them parallel to themselves. Furthermore, the presence of two threaded bolts 8 makes it possible to have two opposed triangles of fixation, independent of one another.

Preferably, as represented in FIG. 2, the stays 13 and 14 are doubled so that there is engagement with each of the flanges of the bars 1 and 2.

What is claimed is:

1. An articulated external fixator for bony parts comprising two bars each having U-shaped profile defining a pair of flanges, the flanges of said bars being formed with a plurality of spaced and aligned holes adapted to receive pins to be inserted in the bony parts, an intermediate piece forming a toggle joint, means for pivotally connecting one end of each of said bars to said intermediate piece, a brace piece attached substantially transverse to said intermediate piece, a pair of stays, means pivotally connecting one end of each of said stays to the end of the brace remote from said intermediate piece, and means for connecting a selected point of each of said stays to a respective bar at a point remote from the one end of the stay connected to said brace.

2. An articulated fixator as in claim 1 wherein said means for connecting the bars to said intermediate piece comprises a removable fastener means for at least one of said bars.

3. An articulated fixator as in claim 2 wherein said fastener means comprises a nut and a bolt.

4. An articulated fixator as in claim 1 wherein said means for connecting each said bar to said intermediate piece comprises a removable fastener means.

5. An articulated fixator as in claim 1 wherein said means for pivotally connecting the stays to said brace piece comprises a removable fastener means for at least one of said bars.

6. An articulated fixator as in claim 5 wherein said removable fastener means comprises a nut and bolt.

7. An articulated fixator as in claim 1 wherein said means for pivotally connecting each said stay to said brace piece comprises a removable fastener means.

* * * * *